United States Patent
Jalisi

(10) Patent No.: US 7,335,227 B2
(45) Date of Patent: *Feb. 26, 2008

(54) MULTILAYER STENT

(75) Inventor: Marc M. Jalisi, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 443 days.

This patent is subject to a terminal disclaimer.

(21) Appl. No.: 10/618,149

(22) Filed: Jul. 10, 2003

(65) Prior Publication Data

US 2004/0106982 A1 Jun. 3, 2004

Related U.S. Application Data

(62) Division of application No. 09/270,403, filed on Mar. 16, 1999, now Pat. No. 6,620,192.

(51) Int. Cl.
*A61F 2/06* (2006.01)
(52) U.S. Cl. .................................. 623/1.15
(58) Field of Classification Search .............. 623/1.15, 623/1.18, 1.34, 1.44, 1.46; 428/586
See application file for complete search history.

(56) References Cited

U.S. PATENT DOCUMENTS

| | | |
|---|---|---|
| 4,538,622 A | 9/1985 | Samson et al. |
| 4,917,104 A | 4/1990 | Rebell |
| 4,925,445 A | 5/1990 | Sakamoto et al. |
| 5,069,217 A | 12/1991 | Fleischhacker, Jr. |
| 5,069,226 A | 12/1991 | Yamauchi et al. |
| 5,171,383 A | 12/1992 | Sagaye et al. |
| 5,213,111 A | 5/1993 | Cook et al. |
| 5,230,348 A | 7/1993 | Ishibe et al. |
| 5,238,004 A | 8/1993 | Sahatjian et al. |
| 5,253,653 A | 10/1993 | Daigle et al. |

(Continued)

FOREIGN PATENT DOCUMENTS

EP    0 795 304    9/1997

(Continued)

OTHER PUBLICATIONS

International Search Authority communication, "International Search Report" dated Jul. 20, 2000.

(Continued)

*Primary Examiner*—(Jackie) Tan-Uyen Ho
(74) *Attorney, Agent, or Firm*—Finnegan, Henderson, Farabow, Garrett & Dunner, L.L.P.

(57) ABSTRACT

A composite stent having a substrate tube made of stainless steel, a nickel-cobalt-chromium-molybdenum alloy, or chonichrome with at least one metal cladding tube is disclosed. Specifically, the substrate tube is placed within a metal cladding tube made of platinum, gold, tantalum, tungsten, platinum-iridium, palladium, or nickel-titanium, preferably with an interference fit therebetween. The composite, laminate tube then undergoes a series of rolling or cold drawing processes interspersed with heat treating to release built up stresses. When the final diameter of the laminate tube is reached, the cladding has been laminated to the exterior of the substrate tube by a bond generated from the rolling and/or cold drawing operations. The finished laminate tube is then cut by laser cutting or chemical etching to form a suitable stent pattern.

20 Claims, 3 Drawing Sheets

U.S. PATENT DOCUMENTS

| | | | |
|---|---|---|---|
| 5,341,818 A | 8/1994 | Abrams et al. | |
| 5,423,849 A | 6/1995 | Engelson et al. | |
| 5,506,059 A | 4/1996 | Robbins et al. | |
| 5,514,154 A * | 5/1996 | Lau et al. | 623/1.15 |
| 5,520,194 A | 5/1996 | Miyata et al. | |
| 5,588,443 A | 12/1996 | Davidson | |
| 5,607,463 A | 3/1997 | Schwartz et al. | |
| 5,628,787 A | 5/1997 | Mayer | |
| 5,630,840 A | 5/1997 | Mayer | |
| 5,636,641 A | 6/1997 | Fariabi | |
| 5,637,089 A | 6/1997 | Abrams et al. | |
| 5,647,858 A | 7/1997 | Davidson | |
| 5,664,580 A | 9/1997 | Erickson et al. | |
| 5,690,644 A | 11/1997 | Yurek et al. | |
| 5,695,111 A | 12/1997 | Nanis et al. | |
| 5,720,300 A | 2/1998 | Fagan et al. | |
| 5,725,570 A | 3/1998 | Heath | |
| 5,725,572 A | 3/1998 | Lam et al. | |
| 5,733,326 A | 3/1998 | Tomonto et al. | |
| 5,824,056 A | 10/1998 | Rosenberg | |
| 5,824,077 A | 10/1998 | Mayer | |
| 5,843,166 A | 12/1998 | Lentz et al. | |
| 5,858,556 A | 1/1999 | Eckert et al. | |
| 5,891,191 A | 4/1999 | Stinson | |
| 5,922,020 A * | 7/1999 | Klein et al. | 623/1.15 |
| 6,174,329 B1 | 1/2001 | Callol et al. | |
| 6,264,687 B1 | 7/2001 | Tomonto | |
| 6,355,058 B1 | 3/2002 | Pacetti et al. | |
| 6,380,457 B1 | 4/2002 | Yurek et al. | |
| 6,475,234 B1 * | 11/2002 | Richter et al. | 623/1.15 |
| 6,755,855 B2 | 6/2004 | Yurek et al. | |

FOREIGN PATENT DOCUMENTS

| | | |
|---|---|---|
| EP | 1 290 984 A2 | 9/1997 |
| EP | 0 824 900 A2 | 2/1998 |
| WO | WO 98/31304 | 7/1998 |

OTHER PUBLICATIONS

U.S. Appl. No. 09/259,808; filed Feb. 26, 1999; Inventor William J. Boyle.

* cited by examiner

US 7,335,227 B2

MULTILAYER STENT

RELATED APPLICATIONS

This is a divisional application of parent application having U.S. Ser. No. 09/270,403, filed Mar. 16, 1999, now U.S. Pat. No. 6,620,192 the contents of which are hereby incorporated by reference.

BACKGROUND OF THE INVENTION

The present invention relates to expandable intraluminal vascular devices, generally referred to as stents. More precisely, the present invention is directed to stents that have a metallic cladding for improved expansion characteristics and radiopacity.

Stents are used to maintain patency of vessels in the body, such as a patient's arteries. A variety of delivery systems have been devised that facilitate the placement and deployment of stents. The stent is initially manipulated while in its contracted or unexpanded state, wherein its reduced diameter more readily allows it to be introduced into the body lumen, such as a coronary artery, and maneuvered into the target site where a lesion has been dilated. Once at the target site, the stent is expanded into the vessel wall to allow fluid to flow through the stent, thus performing a scaffolding function. Stents are usually mounted on balloon catheters and advanced to a lesion site by advancing the catheter. At the site, the stent is expanded by inflating the balloon on which the stent is mounted. Deflation of the balloon and removal of the catheter leave the stent implanted in the vessel in an expanded state. It is also possible to dilate a vascular lesion and deploy a stent at the same time using the same expandable member or inflatable balloon. This variation of the procedure described above obviates the need for a separate balloon dilation catheter and stent deployment catheter.

Stents are typically formed from biocompatible metals such as stainless steel, nickel-titanium, tantalum, and the like, to provide sufficient hoop strength to perform the scaffolding function of holding the patient's vessel open. Also, stents have minimal wall thickness in order to minimize blood flow blockage. But stents can sometimes cause complications including thrombosis, and neointimal hyperplasia by inducement of smooth muscle cell proliferation at the site of implantation of the stent. Such stents typically also do not provide for delivery of localized therapeutic pharmacological treatment of a blood vessel at the location being treated with the stent, which can be useful for overcoming such problems.

In the evolution of stents, there have been developments in the field of stents coated with a layer of polymers. The polymeric materials are typically capable of absorbing and releasing therapeutic drugs. Examples of such stents are disclosed in U.S. Pat. No. 5,443,358 to Eury; U.S. Pat. No. 5,632,840 to Campbell; U.S. Ser. No. 08/842,660, filed Apr. 15, 1997, by J. Yan; and U.S. Ser. No. 08/837,993, filed Apr. 15, 1997, by J. Yan.

Aside from coated stents, there have been developments in the field of multilayer grafts. An example of a multilayer graft is disclosed in U.S. Pat. No. 4,743,252 to Martin, Jr. et al. Martin et al. shows a composite graft having a porous wall structure to permit ingrowth, which graft includes a generally nonporous, polymeric membrane in the wall to prevent substantial fluid passage therethrough so as to provide an implantable porous graft that does not require preclotting prior to implantation. Grafts are known which have multiple layers for strength reinforcement. For example, U.S. Pat. No. 5,282,860 to Matsuno et al. discloses a stent tube comprising an inner tube and an outer polyethylene tube with a reinforcing braided member fitted between the inner tube and the outer tube. The inner tube is made of a fluorine-based resin.

U.S. Pat. No. 5,084,065 to Weldon et al. discloses a reinforced graft assembly made from a vascular graft component and a reinforcing sleeve component. The reinforcing sleeve component may include one or more layers. The second component of the two component system includes the reinforcing sleeve component. Like the graft component, the reinforcing component includes a porous surface and a porous subsurface. Specifically, the reinforcing sleeve component includes multiple layers formed from synthetic, biologic, or biosynthetic and generally biocompatible materials. These materials are typically biocompatible polyurethane or similar polymers.

Despite progress in the art, there is presently no stent available that has a metallic cladding for improved strength reinforcement, expansion characteristics and radiopacity. Therefore, there is a need for such a multilayer metallic clad or laminate stent.

SUMMARY OF THE INVENTION

The present invention is directed to a multilayer intracorporeal device, specifically a multilayer or laminate stent that has a metallic substrate and at least one layer of metallic cladding. The cladding is generally joined to the substrate under high pressure resulting in a structure that resists separation or delamination under normal stress. The cladding metal and the base or substrate material form a bond between them during a deep drawing, cold drawing, or co-drawing on a mandrel process. The method of combining two or more layers of different materials allows for the combination of desirable properties of those materials. Typical material properties to be considered for stent design and performance include strength, ductility, and radiopacity. For example, a substrate layer material may be chosen for its strength, a first cladding material chosen for its ductility, and a second cladding material chosen for its radiopacity.

The present invention provides a method of fabricating a stent for implantation within a body lumen, comprising the steps of providing a substrate tube having an outside surface and an inside surface; disposing a first cladding tube about the substrate tube, wherein the first cladding tube includes a metal; joining the first cladding tube to the outside surface of the substrate tube to form a laminate tube; and forming a stent pattern in the laminate tube to provide for expansion of the stent. In a preferred embodiment, the substrate tube includes a metal selected from the group consisting of stainless steel, a nickel-cobaltchromium-molybdenum alloy, or chonichrome; and the first cladding tube includes a radiopaque metal, preferably selected from the group consisting of platinum, gold, tantalum, tungsten, platinum-10% iridium, or palladium. It may also be desirable to have a substrate tube of a psuedoelastic alloy such as NiTi. A substrate tube from such an alloy can provide mechanical characteristics which facilitate expansion of a stent within a patient's vessels and minimize trauma to the vessels, particularly in indications such as carotid artery treatment.

Joining the first cladding tube to the outside surface of the substrate tube can include rolling and drawing the laminate tube to bond or secure the first cladding tube to the substrate tube. This process is known in the art as deep drawing, cold drawing, or co-drawing on a mandrel. Concurrent or in series with the cold drawing process, the laminate tube can be heat treated or annealed to release stress build-up from the cold working. The bond between the substrate tube and the first cladding tube can be mechanical in whole or in part.

In an alternative method, the present invention further includes disposing a second cladding tube about the first cladding tube; and joining the second cladding tube to the first cladding tube. As a result, the finished stent has two cladding layers laminated on the tubular substrate. Typically, the second cladding layer will be made of a radiopaque metal, preferably including a metal selected from the group consisting of platinum, gold, tantalum, tungsten, platinum-iridium, or palladium. A preferred platinum-iridium alloy is a platinum-10% iridium alloy.

The present invention further contemplates a device which is preferably produced by the above methods, i.e. a stent for implantation within a body lumen having a substrate tube with an exterior surface; a metallic cladding bonded under pressure about the exterior surface of the substrate tube; and a stent pattern formed in the substrate tube and the metallic cladding. In a preferred embodiment, the cladding includes a radiopaque metal, preferably selected from the group consisting of platinum, gold, tantalum, tungsten, platinum-iridium, or palladium. Furthermore, the substrate tube generally includes a metal selected from the group consisting of stainless steel, a nickel-cobalt-chromium-molybdenum alloy, or chonichrome. The substrate tube can also include a superelastic or superelastic alloy such as NiTi.

In particular, it has been found that for the substrate tube, materials such as 316L stainless steel, nickel-cobalt-chromium-molybdenum alloys such as MP35N, or cobalt-chromium-tungsten-nickel-iron alloys such as L605, (chonichrome) are preferable. For the cladding tube, it has been found that platinum, gold, tantalum, tungsten, platinum-10% iridium, or palladium are preferred. Each of the cladding material adds to the performance of the finished laminate tube which would otherwise not be possible with a pure 316L stainless steel, MP35N, or chonichrome tube alone. Another benefit of the present invention is that the metal cladded stent can have a desired amount of radiopacity. Indeed, using cladding tubes made of radiopaque alloys or metals such as platinum, gold, tantalum, or platinum-iridium increases the radiopacity of the stent to assist the cardiologist in tracking the stent during implantation.

The present invention can additionally benefit from use of a substrate or cladding tube made from nickel-titanium, which is a shape memory alloy which can exhibit superelastic properties. With a higher deformation rate due to a nickel-titanium cladding tube, the laminate stent eliminates the need for higher pressure balloons and as a result, the risk of injury to the vessel walls is reduced. The nickel-titanium eases the expansion of the stent in normal temperatures and contraction in relatively elevated temperatures. Where a superelastic alloy such as NiTi is used as a cladding layer in combination with a non-radiopaque high strength alloy substrate such as stainless steel, MP35N or L605, it is generally preferred to include a second cladding layer or tube of a radiopaque metal such as those described above. In this way, the desired mechanical characteristics of the stent can be achieved with the appropriate combination of substrate and first cladding materials, and radiopacity is added to the stent by the second cladding layer or tube.

These and other advantages of the present invention will become apparent from the following detailed description thereof when taken in conjunction with the accompanying exemplary drawings.

DETAILED DESCRIPTION OF THE PREFERRED EMBODIMENTS

Figure 1:
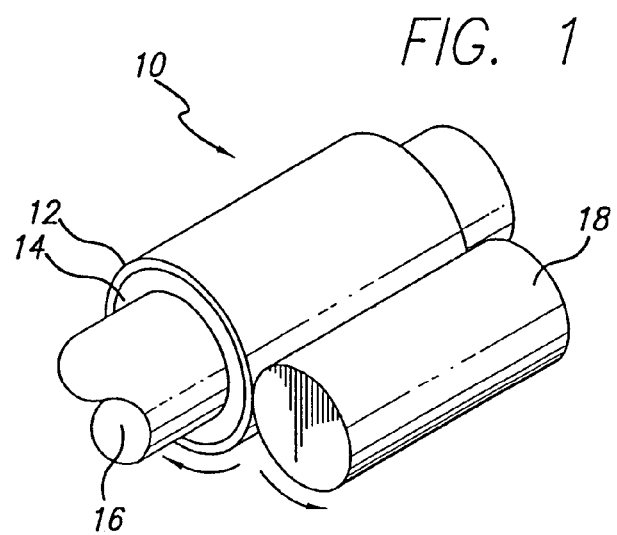
FIG. 1 is a perspective view of a preferred embodiment stent with a tubular cladding mounted on a mandrel, and undergoing compression applied by an external roller.

FIG. 1 is a perspective view of a preferred embodiment of a laminate tube having features of the present invention. As seen in this simplified view, the present invention contemplates creation of laminate tube 10 by joining metal cladding tube 12 to an exterior surface of substrate tube 14. Fundamental to this joining process is first defining the initial diameters of metal cladding tube 12, which should already be in a tubular configuration as seen in FIG. 1, and of substrate tube 14. Tubes 12, 14 can be made by conventional fabrication processes, such as drawing, rolling sheet stock and welding the seam, etc. During these preliminary steps, the diameters and wall thickness of tubes 12 and 14 are selected and set.

In the preferred embodiment of the present invention, there should be an interference fit between the outside diameter of substrate tube 14 and the inside diameter of metal cladding tube 12. The interference fit prevents unwanted, relative shifting between substrate tube 14 and the concentrically disposed cladding tube 12. It is further preferable that the wall thickness of substrate tube 14 be greater than the wall thickness of metal cladding tube 12. The initial wall thicknesses can be important, because the present invention processes encompass a co-drawing or cold drawing operation that reduces the diameter and wall thickness of each tube while increasing its length. To maintain continuous contact at the interface between the interior of metal cladding tube 12 and the exterior of substrate tube 14, it is preferable that the initial wall thicknesses of the respective parts be as described above.

The volumes of metal cladding tube 12 and substrate tube 14 are conserved throughout the various cold drawing stages of diameter reduction. Because the outer tube has a larger surface area than the inner tube, its initial wall thickness must be thinner than the initial wall thickness of the inner tube in order to obtain a decrease in diameter proportionate to the inner tube. In this way, the respective diameters of tubes 12, 14 and their wall thicknesses are reduced proportionately and their lengths increased identically thus minimizing the chance of delamination.

In the preferred embodiment of FIG. 1, metal cladding tube 12 is made from a radiopaque material such as platinum, gold, tantalum, tungsten, platinum-iridium alloy, or palladium. Substrate tube 14 is preferably made from a material such as stainless steel including 316L, a nickelcobalt-chromium-molybdenum alloy such as MP35N, or from a chonichrome such as L605. MP35N is a trade name for a metal alloy comprising 35% nickel, 33.2% cobalt, 20% chromium, 9.53% molybdenum, and trace amounts of other elements. L605 is a trade name for a metal alloy comprising 50.5% cobalt, 20% chromium, 15.28% tungsten, 9.8% nickel, and trace amounts of iron and other elements. The aforementioned materials facilitate consistent tube diameter and wall thickness reduction while minimizing the chance of delamination of the concentric tubes. Of course reversing the material selection for the substrate tube and the cladding tube in specific applications is also contemplated. In addition, a substrate tube containing a superelastic alloy such as NiTi can also be used.

Laminate tube 10 comprising of metal cladding tube 12 over substrate tube 14 is optionally mounted on mandrel 16 and rolled by application of external pinching pressure through roller 18. This is represented in the perspective view of FIG. 1. Along with the rolling operation depicted in FIG. 1, the present invention contemplates a co-drawing or cold drawing operation shown in the perspective view of FIG. 2. Here, laminate tube 10 with metal cladding tube 12 surrounding substrate tube 14 is shown prior to passing through opening 20 of die 22. By passing through a series of dies 22 with sequentially decreasing opening diameters, it is possible to deep draw laminate tube 10 to the final desired diameter. As the name suggests, this cold drawing process is preferably carried out at room temperature, below the recrystallization temperatures of the tube materials. By repeating the operations shown in FIGS. 1 and 2, it is possible to reduce laminate tube 10 from a starting outside diameter of, for example, about 0.5 inch down to about 0.06 inch. The starting wall thickness for the laminate tube 10 is about 0.03 to about 0.065 inches and is reduced down to about 0.003 inch.

In a preferred embodiment process, the rolling and cold drawing operations are repeated to achieve a maximum of 25 percent in reduction of surface area, to be followed by a heat treating step to release built up internal stresses. Without the heat treating step, there is a possibility that the deformations are sufficient to exceed the ultimate yield strength of the materials thereby causing ruptures or cracks. Each sequence of operations slowly reduces the diameter of composite stent while proportionately increasing its length.

Although the rolling and cold drawing processes of the present invention 20 are conducted at room temperature, the pressures involved may cause the temperature between metal cladding tube 12 and substrate tube 14 to elevate sufficiently to facilitate a mechanical bond which is typically created between the two adjacent layers. In this manner, metal cladding tube 12 is permanently attached to substrate tube 14 and delamination of the two materials is minimized under normal operating conditions for the stent. It is desireable to eliminate delamination between the two or more layers entirely. Preferably, the material used as substrate tube 14 has a smaller coefficient of thermal expansion than the material used for the cladding tube 12. This facilitates maintaining contact between the two tubes 12 and 14 during the rolling and cold drawing processes and prevents delamination of the tubes subsequent thereto.

In a preferred method, laminate tube 10 undergoes about a twenty-five percent (25%) diameter reduction from the rolling or cold drawing operations. This is accomplished by passing laminate tube 10 through a series of dies 22 with each die reducing the diameter by preferably one percent (1%). With a series of twenty-five dies 22, it is possible to achieve the twenty-five percent (25%) diameter reduction.

Laminate tube 10 then undergoes a heat treat process to release stress and to eliminate restrained dislocations. Next, laminate tube 10 undergoes another twenty-five percent (25%) diameter reduction by cold drawing or rolling, followed by another heat treating process. This cycle is repeated until the desired diameter of laminate tube 10 is reached. Throughout the present invention process, laminate tube 10 may optionally undergo anneal cycles in order to impart desired material properties such as ductility, strength, etc. Through the present invention process, it has been observed that the finished laminate tube 10 has a straightness of 0.02 inch per inch for a six to twelve inch length tube. When the final diameter is reached, the laminate tube is cut to length.

Laminate tube 10 is further processed to form a stent pattern therein such as illustrated by stent 40 in FIGS. 5 and 6 discussed below. One method for forming such a stent pattern is by chemical etching. Such a process is disclosed in, for example, U.S. Pat. No. 5,735,893 to Lau et al., entitled "Expandable Stents and Method for Making Same," the contents of which is hereby incorporated by reference. Alternatively, a stent pattern may be formed by a laser cutting process. Such a process is shown and disclosed in, for example, U.S. Pat. No. 5,759,192 to Saunders, entitled "Method and Apparatus for Direct Laser Cutting of Metal Stents," the contents of which is hereby incorporated by reference.

Figure 3:
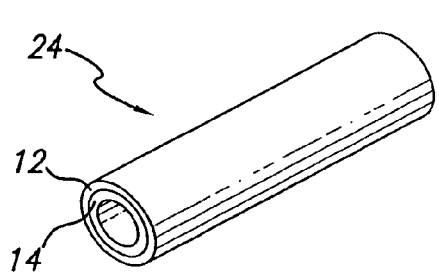
FIG. 3 is a perspective view of a preferred embodiment metallic clad stent having struts formed therein.

FIG. 3 is a perspective view of a finished laminate tube 24 having metal cladding tube 12 laminated to substrate tube 14. The thickness of a single wall of the metal cladding tube 12 is about 0.0001 to about 0.010 inches, preferably about 0.0005 to about 0.004 inches. The thickness of a single wall of the substrate tube 14 is about 0.0001 to about 0.010 inches, preferably about 0.001 to about 0.004 inches. The material of the substrate tube 14 is preferably 316L stainless steel, but can also be other types of stainless steel, MP35N, L605 or superelastic alloys such as NiTi. The material of the metal cladding tube 12 is preferably platinum-10% iridium, but can also be gold, tantalum, platinum, palladium, tungsten or the like.

Figure 4:
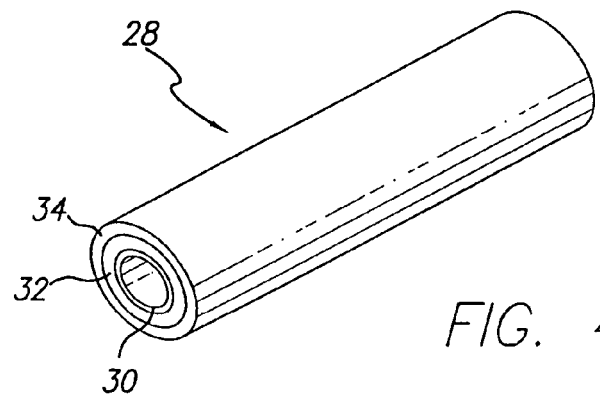
FIG. 4 is a perspective view of an alternative embodiment stent having multiple cladding layers with the stent struts formed therein.

FIG. 4 provides a perspective view of an alternative embodiment of a laminate tube 28 having substrate tube 30 that is laminated with first metallic cladding tube 32. Second metallic cladding tube 34 is laminated to the outer surface of first metallic cladding tube 32. The thickness of a single wall of the substrate tube 30 is about 0.0001 to about 0.010 inches, preferably about 0.001 to about 0.004 inches. The thickness of a single wall of the first metallic cladding tube 32 is about 0.0001 to about 0.002 inches, preferably about 0.0005 to about 0.001 inches. The thickness of a single wall of the second metallic cladding tube 34 is about 0.0001 to about 0.002 inches, preferably about 0.0005 to about 0.001 inches. The material of the substrate tube 30 is preferably 316L stainless steel, but can also be other types of stainless steel, MP35N, L605, NiTi or the like or any suitable radiopaque metal such as those discussed above. The material of the first cladding tube 32 is preferably NiTi, but can also be stainless steel, MP35N, L605 or the like, or any suitable radiopaque metal such as those discussed above. The material of the second metallic cladding tube 34 is preferably platinum-10% iridium, but can also be any other suitable radiopaque metal such as those discussed above, or a superelastic alloy such as NiTi, or a high strength metal or alloy such as stainless steel, MP35N, L605 or the like.

Figure 2:
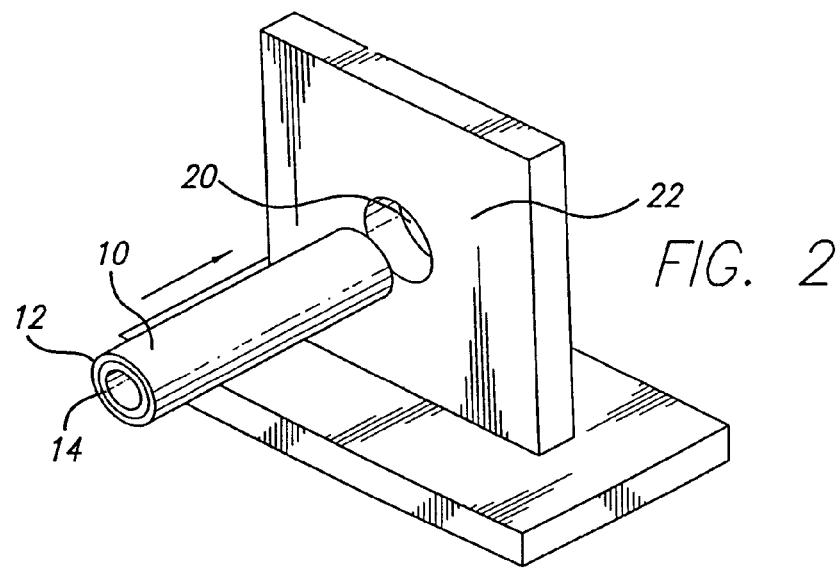
FIG. 2 is a perspective view of a deep drawing operation showing the present invention stent prior to passing through a die.

The multiple layers of cladding of laminate tube 28 are created as previously described in connection with FIGS. 1 and 2, except that second metallic cladding tube 34 is added to the outside surface of first metallic cladding tube 32. The three tubes 30, 32, 34 then undergo the rolling or cold drawing, and heat treating operations as described previously. When the final diameter is reached, laminate tube 28 is cut to the desired length and processed to form a stent pattern.

As previously discussed, one typical metallic cladding or substrate material is superelastic or pseudoelastic nickel-titanium (NiTi) alloy. Because nickel-titanium is a superelastic or shape memory alloy, it is possible to create a stent that reverts to various formations based on the ambient temperature and applied stress. In one example, a NiTi-clad stent is formed full size but deformed (i.e., compressed) into a smaller diameter onto the balloon of a delivery catheter to facilitate transfer to the intended intraluminal site. The stress induced by the deformation transforms the stent from an austenitic phase to a martensitic phase. Upon release of the restraining force, when the stent reaches the desired site, the stent self-expands isothermally by transformation back to the austenitic phase. Similarly, for shape memory NiTi alloys, the metal transforms from the martensitic to the austenitic phase upon application of heat, such as exposure to body temperature, resulting in self-expansion of the cladding material. The behavior of such superelastic alloys and their processing are well known in the art. Certainly a benefit is that the nickel-titanium eases the expansion of the stent in normal body temperatures. In a preferred embodiment, if the cladding includes a radiopaque metal such as gold, platinum, tantalum, platinum-iridium alloy, the radiopacity of the stent is improved. Accordingly, the present invention can have enhanced performance or expansion characteristics as well as improved visibility for the cardiologist.

Figure 5:
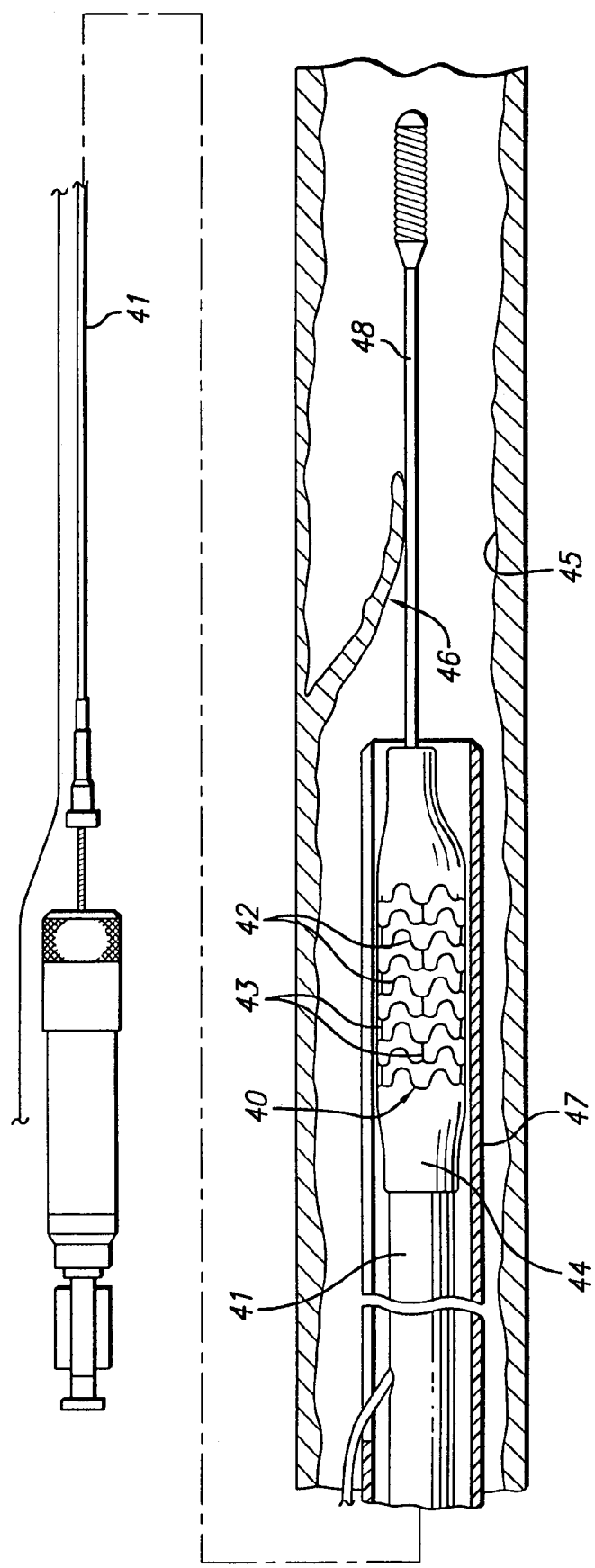
FIG. 5 is an elevational view in partial section of a delivery catheter within an artery with a laminate stent having features of the invention disposed about the delivery catheter.

In FIG. 5 a laminate stent 40 incorporating features of the invention is illustrated mounted on a delivery catheter 41. The laminate stent 40 generally has a plurality of radially expandable cylindrical elements 42 disposed generally coaxially and interconnected by elements 43 disposed between adjacent cylindrical elements. The delivery catheter 41 has an expandable member or balloon 44 for expanding the laminate stent 40 within an artery 45. The artery 45, as shown in FIG. 5, has a dissected lining 46 which has occluded a portion of the arterial passageway.

A laminate stent 40 can have an outside diameter of up to about 0.1 inch in the unexpanded condition, preferably, about 0.05 to about 0.07 inches. The laminate stent 40 can be expanded to an outside diameter of about 0.06 to about 0.3 inches or more, preferably about 0.1 to about 0.2 inches, when deployed in a body lumen. The length of the laminate stent 40 prior to expansion is about 10 to about 50 mm, preferably about 15 to about 25 mm. In addition, multiple laminate stents 40 can be connected in order to create a stent with an effective length of any multiple of the previously discussed lengths. Thus, 2, 3, 4, 5 or more laminate stents 10 can be connected in order to create a stent with a longer effective length.

The delivery catheter 41, onto which the stent 40 is mounted, can be essentially the same as a conventional balloon dilatation catheter used for angioplasty procedures. The balloon 44 may be formed of suitable materials such as polyethylene, polyethylene terephthalate, polyvinylchloride, nylon and ionemers such as Surlyn™ manufactured by the polymer products division of the DuPont Company. Other polymers may also be used. In order for the laminate stent 40 to remain in place on the balloon 44 during delivery to the site of the damage within the artery 45, the laminate stent 40 is compressed onto the balloon. A retractable protective delivery sleeve 50 as described in co-pending applications Ser. No. 07/647,464 filed on Apr. 25, 1990 and entitled STENT DELIVERY SYSTEM may be provided to further ensure that the stent stays in place on the expandable portion of the delivery catheter 41 and prevent abrasion of the body lumen by the open surface of the stent 40 during delivery to the desired arterial location. Other means for securing the laminate stent 40 onto the balloon 44 may also be used, such as providing collars or ridges on the edges of the working portion, i.e., the cylindrical portion, of the balloon.

Each radially expandable cylindrical element 42 of the laminate stent 40 may be independently expanded. Therefore, the balloon 44 may be provided within an inflated shape other than cylindrical, e.g., tapered, to facilitate implantation of the laminate stent 40 in a variety of body lumen shapes.

In a preferred embodiment, the delivery of the laminate stent 40 is accomplished in the following manner. The laminate stent 40 is first mounted onto the inflatable balloon 44 on the distal extremity of the delivery catheter 41. The balloon 44 is slightly inflated to secure the laminate stent 40 onto the exterior of the balloon. The catheter/stent assembly is introduced within the patient's vasculature in a conventional Seldinger technique through a guiding catheter 47. A guide wire 48 is disposed across the damaged arterial section with the detached or dissected lining 46 and then the catheter/stent asserhbly is advanced over a guide wire 48 within the artery 45 until the laminate stent 40 is directly under the detached lining 46. The balloon 44 of the catheter is expanded, expanding the laminate stent 40 against the artery 45.

The laminate stent 40 serves to hold open the artery 45 after the catheter 41 is withdrawn. Due to the formation of the laminate stent 40 from an elongated laminate tube, the undulating component of the cylindrical elements of the laminate stent 10 is relatively flat in transverse cross-section, so that when the stent is expanded, the cylindrical elements are pressed into the wall of the artery 45 and as a result do not interfere with the bloodflow through the artery 45. The cylindrical elements 42 of the laminate stent 40 which are pressed into the wall of the artery 45 will eventually be covered with endothelial cell growth which further minimizes bloodflow interference. The undulating portion of the cylindrical sections 42 provide good tracking characteristics to prevent stent movement within the artery. Furthermore, the closely spaced cylindrical elements 42 at regular intervals provide uniform support for the wall of the artery 45, and consequently are well adopted to tack up and hold in place small flaps or dissections in the wall of the artery 45.

Figure 6:
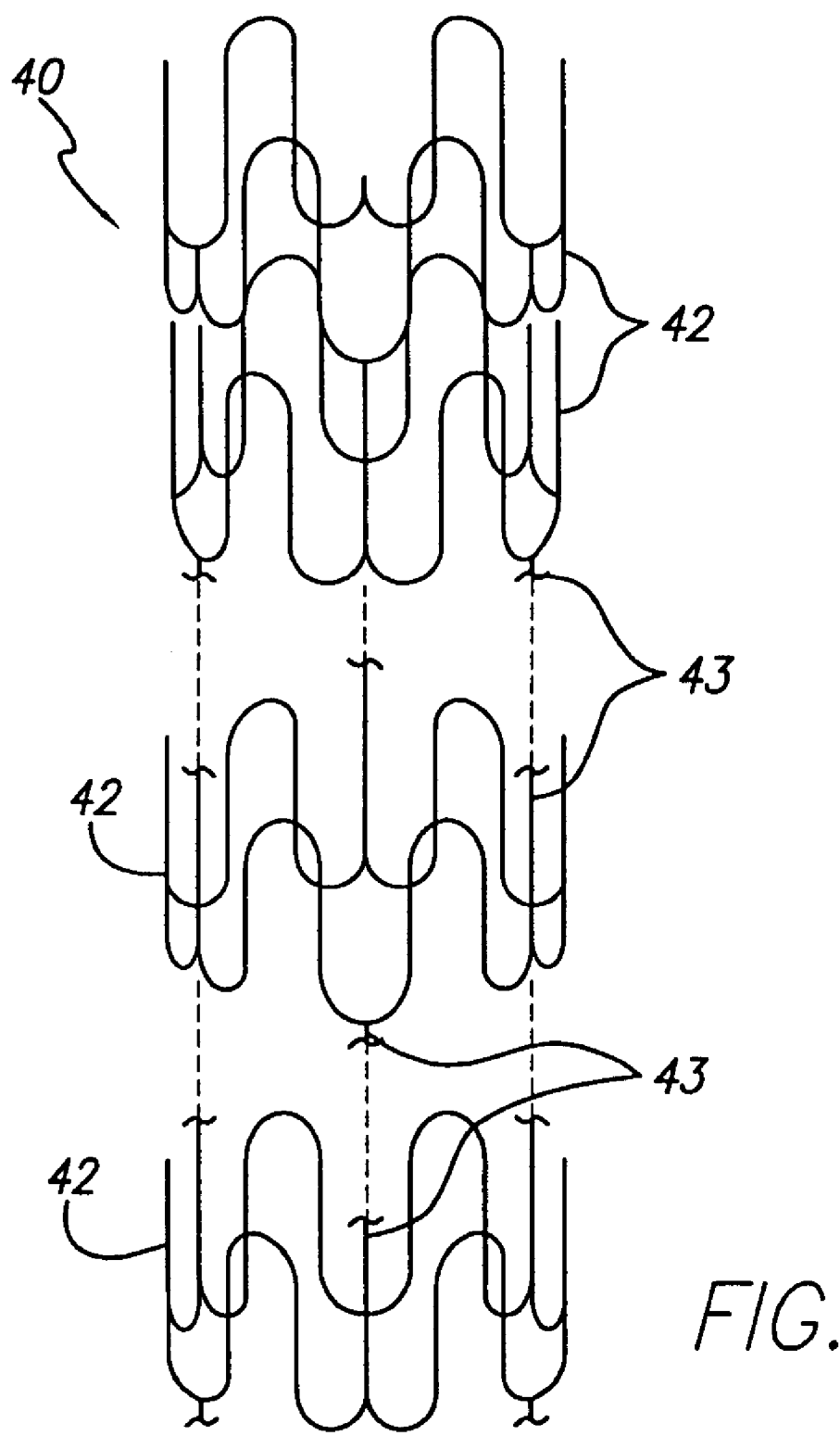
FIG. 6 is a perspective view of a laminate stent having features of the invention.

FIG. 6 is an enlarged perspective view of the laminate stent 40 shown in FIG. 5 with one end of the stent shown in an exploded view to illustrate in greater detail the placement of interconnecting elements 43 between adjacent radially expandable cylindrical elements 42. Each pair of interconnecting elements 43 on one side of cylindrical elements 42 are preferably placed to achieve maximum flexibility for a stent. In the embodiment shown in FIG. 6, the laminate stent 40 has three interconnecting elements 43 between adjacent radially expandable cylindrical elements 42 which are 120° apart. Each pair of interconnecting elements 43 of one side of a cylindrical elements 42 are offset radially 60° from the pair on the other side of the cylindrical element. The alternation of the interconnecting elements result in a stent which is longitudinally flexible in essentially all directions. Various configurations for the placement of interconnecting elements 43 are possible. In addition, while the expandable cylindrical elements 42 and interconnecting elements 43 have been shown in the stent pattern depicted in FIGS. 5 and 6, any suitable stent pattern that allows for a desired amount of expansion and radial strength for a given application is also contemplated. For example, the laminate tubes 10, 24 and 28 could have any of a number of mesh-like or spiral stent patterns formed thereon.

While particular embodiments of the present invention have been illustrated and described, it is apparent to those skilled in the art that various modifications can be made without departing from the spirit and scope of the invention. Any of a variety of stent designs and applications can benefit from the present invention. Accordingly, it is not intended that the present invention be limited except by the appended claims.

What is claimed:

1. A laminate stent for implantation within a body lumen, comprising:
    a substrate tube formed from a superelastic alloy and having an exterior surface;
    a first cladding layer formed from a metallic material and bonded to the exterior surface of the substrate tube;
    a second metallic radiopaque cladding layer bonded to the first layer thereby forming a laminate tube; and
    a stent pattern formed in the laminate tube such that the resultant laminate stent includes a plurality of radially expandable cylindrical elements disposed generally coaxially and interconnected by elements disposed between adjacent cylindrical elements, the cylindrical elements and the interconnecting elements being entirely formed of the substrate tube, the first cladding layer, and the second metallic radiopaque cladding layer.

2. The laminate stent of claim 1, wherein the superelastic alloy of the substrate tube is nickel-titanium.

3. The laminate stent of claim 1, wherein the wall thickness of the second metallic radiopaque cladding layer is less than the wall thickness of the metallic substrate tube.

4. The laminate stent of claim 1, wherein the substrate tube has a coefficient of thermal expansion that is less than a coefficient of thermal expansion of the first cladding layer.

5. The laminate stent of claim 1, wherein the first cladding layer is a metal selected from the group consisting of stainless steel, nickel-cobalt-chromium-molybdenum alloy and chonichrome.

6. The laminate stent of claim 5, wherein the first cladding layer is a nickel-cobalt-chromium-molybdenum alloy comprising about 35% nickel, about 33% cobalt, about 20% chromium, and about 10% molybdenum.

7. The laminate stent of claim 5, wherein the first cladding layer is a metal alloy comprising about 50% cobalt, about 20% chromium, about 15% tungsten, and about 10% nickel.

8. The laminate stent of claim 1, wherein the second metallic radiopaque cladding layer is a metal selected from the group consisting of platinum, gold, tantalum, tungsten, a platinum-iridium alloy, and palladium.

9. The laminate stent of claim 8, wherein the second metallic radiopaque cladding layer is a platinum-10% iridium alloy.

10. The laminate stent of claim 1, wherein the first cladding layer is a radiopaque material selected from the group consisting of platinum, gold, tantalum, tungsten, a platinum-iridium alloy, and palladium.

11. The laminate stent of claim 1, wherein the laminate stent has an unexpanded diameter of up to about 0.1 inches.

12. The laminate stent of claim 11, wherein the laminate stent has an unexpanded diameter ranging from about 0.05 inches to about 0.07 inches.

13. The laminate stent of claim 1, wherein the laminate stent has an expanded diameter ranging from about 0.06 inches to about 0.3 inches.

14. The laminate stent of claim 13, wherein the laminate stent has an expanded diameter ranging from about 0.1 inches to about 0.2 inches.

15. The laminate stent of claim 1, wherein the laminate stent has a length ranging from about 10 to 50 mm.

16. The laminate stent of claim 15, wherein the laminate stent has a length ranging from about 15 to 25 mm.

17. The laminate stent of claim 1, wherein each of the plurality of radially expandable cylindrical elements is independently expandable.

18. The laminate stent of claim 1, wherein the substrate tube, the first cladding layer, and the second metallic radiopaque cladding layer are bonded by rolling and cold drawing.

19. The laminate stent of claim 1, wherein the substrate tube, the first cladding layer, and the second metallic radiopaque cladding layer have been heat treated.

20. The laminate stent of claim 1, wherein the stent pattern is performed by a process selected from the group consisting of chemical etching and laser cutting.

* * * * *